United States Patent [19]
Zhong

[11] Patent Number: 5,869,127
[45] Date of Patent: Feb. 9, 1999

[54] METHOD OF PROVIDING A SUBSTRATE WITH A BIO-ACTIVE/BIOCOMPATIBLE COATING

[75] Inventor: Sheng-Ping Zhong, Northboro, Mass.

[73] Assignee: Boston Scientific Corporation, Natick, Mass.

[21] Appl. No.: 877,825

[22] Filed: Jun. 18, 1997

Related U.S. Application Data

[63] Continuation-in-part of Ser. No. 392,141, Feb. 22, 1995, Pat. No. 5,702,754.

[51] Int. Cl.$^6$ .............................. B05D 3/10; B05D 3/00; A61L 33/00
[52] U.S. Cl. ...................... 427/2.12; 427/2.13; 427/2.28; 427/2.3; 427/2.31; 427/333
[58] Field of Search ..................................... 427/333, 2.13, 427/2.12, 2.31, 2.24, 2.28, 2.3, 407.1

[56] References Cited

U.S. PATENT DOCUMENTS

| | | | |
|---|---|---|---|
| 4,069,352 | 1/1978 | Parsons, Jr. | 427/2.13 |
| 4,119,094 | 10/1978 | Micklus et al. | 128/132 R |
| 4,177,038 | 12/1979 | Biebricher et al. | 210/635 |
| 4,500,676 | 2/1985 | Balazs et al. | 427/400 |
| 4,600,652 | 7/1986 | Solomon et al. | 428/423.2 |
| 5,037,677 | 8/1991 | Halpern et al. | 427/338 |
| 5,041,100 | 8/1991 | Rowland et al. | 604/265 |
| 5,049,393 | 9/1991 | Noon et al. | 424/484 |
| 5,061,750 | 10/1991 | Feijen et al. | 424/422 |
| 5,080,924 | 1/1992 | Kamel et al. | 427/333 |
| 5,132,108 | 7/1992 | Narayanan et al. | 424/78.17 |
| 5,133,742 | 7/1992 | Pinchuk | 623/11 |
| 5,163,958 | 11/1992 | Pinchuk | 623/11 |
| 5,225,248 | 7/1993 | Stephenson | 427/333 |
| 5,263,992 | 11/1993 | Guire | 623/66 |
| 5,272,012 | 12/1993 | Opolski | 427/2 |
| 5,282,823 | 2/1994 | Schwartz et al. | 604/198 |
| 5,342,348 | 8/1994 | Kaplan | 604/891.1 |
| 5,342,621 | 8/1994 | Eury | 4/2 |
| 5,350,800 | 9/1994 | Verhoeven et al. | 424/409 |
| 5,360,397 | 11/1994 | Pinchuk | 604/27 |
| 5,383,928 | 1/1995 | Scott et al. | 623/1 |
| 5,389,533 | 2/1995 | von Gentzkow et al. | 435/180 |
| 5,403,750 | 4/1995 | Braatz et al. | 427/207.1 |
| 5,449,382 | 9/1995 | Dayton | 623/1 |
| 5,465,450 | 11/1995 | Buscemi et al. | 623/6 |
| 5,496,581 | 3/1996 | Yianni et al. | 427/2.12 |
| 5,510,443 | 4/1996 | Schaffer et al. | 427/333 |
| 5,541,167 | 7/1996 | Hsu et al. | 514/56 |
| 5,571,166 | 11/1996 | Dinh et al. | 623/1 |
| 5,575,818 | 11/1996 | Pinchuk | 623/1 |
| 5,591,224 | 1/1997 | Schwartz et al. | 623/1 |
| 5,599,352 | 2/1997 | Dinh et al. | 623/1 |
| 5,652,347 | 7/1997 | Pouyanai et al. | 536/18.5 |
| 5,702,754 | 12/1997 | Zhong | 427/2.28 |

FOREIGN PATENT DOCUMENTS

| | | |
|---|---|---|
| 496 305 A2 | 7/1992 | European Pat. Off. . |
| 627 226 A1 | 12/1994 | European Pat. Off. . |
| WO 91/19756 | 12/1991 | WIPO . |
| WO 92/19289 | 11/1992 | WIPO . |
| WO 92/19290 | 11/1992 | WIPO . |

*Primary Examiner*—Diana Dudash
*Attorney, Agent, or Firm*—Hoffman & Baron, LLP

[57] ABSTRACT

Disclosed is a method of enhancing the biocompatibility of a substrate by providing the substrate with a continuous bio-active surface coating. This method includes applying to the substrate a first coating which includes an aqueous dispersion or emulsion of a polymer containing an organic acid functional group and an excess of a polyfunctional cross-linking agent which is reactive with the organic acid groups of the polymer. A continuous bio-active surface coating is then formed over the dried first coating by applying thereover a bio-active agent containing an organic acid functional group or metal salt thereof. The first and second coatings are then dried to covalently bond the organic acid functional groups of the bio-active agent to the polymer through the excess unreacted polyfunctional cross-linking agent.

17 Claims, No Drawings

METHOD OF PROVIDING A SUBSTRATE WITH A BIO-ACTIVE/BIOCOMPATIBLE COATING

CROSS-REFERENCE TO RELATED APPLICATION

This application is a continuation-in-part of U.S. Ser. No. 08/392,141, filed Feb. 22, 1995, now U.S. Pat. No. 5,702,754 which is incorporated by reference herein.

FIELD OF INVENTION

This invention relates generally to bio-active substrate coatings. More particularly, the present invention relates to a method for providing a medical device or a part thereof with a bio-active coating which enhances the antithrombogenic nature of such a device without the use of solvents and/or the need for high temperature curing. Coatings and devices incorporating such coatings are also described.

BACKGROUND OF THE INVENTION

It is generally known to provide a substrate, such as a medical device or parts of such a device with bio-active coatings for the purpose of enhancing the bio-compatibility of the device when it is introduced into a mammal, such as a human body.

Endoprostheses used for minimally invasive procedures in body conduits, such as, for example, in blood vessels may be provided with bio-active coatings. Vascular grafts, stents and graft-stent combinations are specific examples of such endoprostheses. Other useful devices include catheters, guide wires, trocars, introducer sheaths and the like.

Medical articles or devices coated with hydrophilic coatings have been described in a number of references, some of which are discussed below. These patents all employ the use of solvents and/or the requirement for high temperature curing.

U.S. Pat. No. 4,119,094 discloses a method of coating a substrate with a polyvinylpyrrolidone-polyurethane interpolymer. In this method, a polyisocyanate and a polyurethane in a first solvent, such as, methyl ethyl ketone are applied to a substrate. The first solvent is then evaporated and polyvinylpyrrolidone in a second solvent is applied to the treated substrate. The second solvent is then evaporated.

International Patent Applications Nos. PCT/EP92/00918, PCT/EP92/00919 and PCT/DK92/00132 disclose methods for providing medical devices having polyurethane surfaces with a hydrophilic coating of poly(meth)acrylamide. Before application of the hydrophilic coating to the poly(meth)acrylamide substrate surface, it is treated with a compound having functional groups capable of reacting with the polyurethane and the poly(meth)acrylamide, respectively. This compound is typically a di- or higher isocyanate functionality in an organic solvent.

U.S. Pat. No. 5,272,012 discloses a method for applying a protective, lubricious coating to a surface of a substrate. The coating described by the '012 patent includes a protective compound, such as a urethane; a slip additive, such as a siloxane; and an optional cross-linking agent, such as a polyfunctional aziridine. The surface of a substrate coated with such a composition, however, is not continuously lubricious. Such a coating contains separate physical domains of lubriciousness interspersed within a protective matrix, rather than a continuous layer of a lubricious agent.

U.S. Pat. No. 5,037,677 discloses a method of interlaminar grafting of continuous, hydrophilic anti-fogging coatings for acrylic intra-ocular lenses. Such a method is accomplished using at least two laminae which are not mutually soluble. For example, the '677 patent describes preparing a solution of a copolymer of ethyl methacrylate, butyl acrylate and hydroxyethyl methacrylate in an ethoxy ethyl acetate organic solvent. To this solution is added a molar excess of polyisocyanate. This solution is applied to a plexiglass substrate which is placed in a vacuum oven, where a prepolymer is formed from the two solutes while the ethoxyethyl acetate solvent is evaporated. A 0.2% sodium hyaluronate solution is then applied to the surface of the plexiglass. The plexiglass is then returned to an oven wherein the hydroxyl groups of the Na-hyaluronate react with the isocyanate groups in the prepolymer layer. Coatings formed in such a manner as the '677 patent suffer from the drawback that organic solvents and/or other toxic chemicals are used as carriers which, if not completely removed prior to introduction of the substrate into the body, can deleteriously react in vivo to cause inflammation, blood clotting and other undesirable side effects. Thus, in order to avoid the use of such organic solvents, some non-solvent methods have been developed.

For example, EP Patent Application Nos. 92100787.8 and EP 0 496 305 A2 disclose methods for preparing a shaped medical article with a lubricous coating. In these methods, a coating composition that includes a blend of polyurethane and polyvinylpyrrolidone is co-extruded with a substrate polymer to produce a shaped article having on a surface thereof a layer of the coating composition which becomes lubricous when contacted with water.

U.S. Pat. No. 5,041,100 discloses a method for coating a substrate with a mixture of poly(ethylene oxide) and an aqueous dispersion of a structural plastic material, e.g. polyurethane. As an example, this patent discloses a non-cross-linked admixture of poly(ethylene oxide) and a structural plastic material. This composition provides a hydrophilic character to the substrate which may leach to the surface thereof, or be entrapped adjacent to the surface to provide a hydrophilic, reduced friction character thereto, particularly when hydrated.

The methods in the above-described references suffer from the drawback that interpolymer networks which physically attach hydrophilic polymers to their substrates often break down upon prolonged turbulent flow or soaking. Furthermore, the hydrophilic species are weakly attached to their substrates and can be easily washed away, thereby rendering the underlying article insufficiently lubricous.

International Patent Application No. PCT/DK91/00163, co-owned with the present invention, discloses a method of providing a medical instrument with a hydrophilic, low-friction coating. This method includes the steps of (1) forming an inner layer on the substrate from an aqueous polymer emulsion, (2) forming an outer layer on top of the inner layer from an aqueous solution of a water-soluble hydrophilic polymer and (3) curing the two layers simultaneously by heating to a temperature above 100° C.

Although the use of organic solvents is eliminated in this method, high curing temperatures must be applied to bond the inner layer to the outer layer. These high curing temperatures are not useful on heat-sensitive materials, as well as, heat-sensitive biomolecules.

Thus, heat-sensitive substrates, such as poly(ethylene terephthalate) (PET) balloon catheters cannot be used with this material. Moreover, molecules such as nucleic acids, proteins, peptides, hormones, heparin and the like are heat-sensitive biomolecules which cannot be exposed to such high temperatures without losing their activity.

The art is not limited, however, to medical devices having lubricious coatings disposed on a surface thereof. Rather, medical articles or devices coated with bio-compatible or bio-active agents have also been described, some of which are set forth below. All of these patents employ various inefficient and/or harsh methods for attaching the bio-compatible/bio-active agent to the surface of a medical article.

For example, U.S. Pat. No. 5,541,167 describes a thrombo-resistant and defoaming coating for blood contacting surfaces including bubble oxygenators, blood filters, etc. This coating includes a commercial preparation of polydimethylsiloxane and silicon dioxide and a quartemary ammonium complex of heparin, such as stearyldimethylbenzyl. This coating, however, suffers from the drawback that the defoaming and heparin components are dissolved in an organic solvent, such as methylene chloride. Such solvents can denature and reduce the bio-activity of bio-active agent, such as heparin. Furthermore, such organic solvent systems produce environmentally hazardous waste, as well as attacking certain polymer substrates.

In a different approach to rendering an implantable medical device bio-compatible, U.S. Pat. No. 5,360,397 describes a porous bio-compatible and bio-stable polyurethane mesh for a catheter made from polycarbonate urethane. This mesh is sputter coated and/or impregnated with a bio-active agent, such as for example, a bactericide. A catheter treated in such a manner, however, is imparted with transient bio-activity at best because the bio-active agent is not covalently bound to the surface thereof. Furthermore, the process of making such a catheter is inefficient because the porous polyurethane mesh must be attached to the surface of the catheter prior to the application of the bio-active agent.

Still further, U.S. Pat. No. 5,263,992 describes a medical device having a bio-compatible coating which includes a bio-compatible agent, such as for example, heparin or streptokinase and a chemical linking moiety. This chemical linking moiety has a structure represented by: A-X-B, wherein A is a photochemically reactive group, B is a reactive group which responds to a different stimulus than A and X is a non-interfering skeletal moiety, such as a $C_1$–$C_{10}$ alkyl. The bio-compatible agent is covalently linked to the surface of the medical device via the linking moiety. In particular, the photochemically reactive group (A) when activated covalently binds to the surface of the medical device. The remaining unreacted reactive group (B) when activated covalently binds to the bio-compatible agent and anchors it to the surface of the medical device. Such devices, however, are difficult and inefficient to produce because they require the use of two separate stimuli to activate the A and B groups of the chemical linking moiety, respectively. Furthermore, the UV light used to activate the A group of the chemical linking moiety for covalently binding it to the surface of a medical device can denature bio-active agents. Such denaturization reduces the bio-activity of such agents and can result in undesirable medical outcomes, such as, clot formation in the case of an anti-thrombogenic agent.

The present invention, however, is directed to a method of providing a substrate, particularly a medical device, or a part of such device, intended for introduction in the human body, with a bio-active coating which enhances the bio-compatibility of the substrate. This method is particularly advantageous because it makes it possible to coat devices which are sensitive to high processing temperatures, such as (PET) balloon catheters and other polymeric or heat sensitive materials or biomolecules. Moreover, the present invention discloses the use of two-component bio-compatible coatings which are both aqueous based. Such coatings are mutually soluble and do not pose the increased medical risks associated with coatings containing organic solvents. Furthermore, preparation of the present aqueous coatings is more efficient because vacuum baking substrates is not required as there are no organic solvents that must be removed. Moreover, because the bio-active surface is covalently bonded to the polymer of the first coating, this coating is permanently attached to the substrate unlike certain of the transient coatings discussed above.

In summary, the prior art methods suffer from the drawback that they use organic solvents in their coating layer and/or cure at high temperatures, are transient or inefficient to produce. Thus, there is a need for improved bio-active agent/bio-compatible coatings which enhance the compatibility and abrasion-resistance of the surface of heat sensitive medical devices. In particular, there is a need for improved compositions and devices which have antithrombogenic properties and more efficient methods of providing same. The present invention is directed to meeting these and other needs.

SUMMARY OF THE INVENTION

In one embodiment of the present invention there is provided a method of enhancing the biocompatibility of a substrate by providing the substrate with a continuous bio-active surface coating. This method includes applying to the substrate a first coating which includes an aqueous dispersion or emulsion of a polymer containing an organic acid functional group and an excess of a polyfunctional cross-linking agent which is reactive with the organic acid groups of the polymer. This coating is then permitted to dry in order to cross-link and render the first coating substantially water-insoluble. Excess unreacted polyfunctional cross-linking agent remains present in the cross-linked first coating. A continuous bio-active surface coating is then formed on the first coating by contacting the dried first coating layer with a second coating of an aqueous solution or dispersion of a bio-active agent or a derivative thereof which contain an organic acid functional group or metal salt thereof. The first and second coatings are then dried to covalently bond the organic acid functional groups of the bio-active agent to the polymer through the excess unreacted polyfunctional cross-linking agent.

In another embodiment of the present invention, there is provided a medical device having a bio-active coating on at least a portion of a surface thereof. This bio-active coating includes a first substantially water-insoluble coating layer formed from an aqueous dispersion or emulsion of an organic acid functional group-containing polymer and an excess of a polyfunctional cross-linking agent which is reactive with the organic acid groups on the polymer. This composition also includes a second coating of an aqueous solution or dispersion of a bio-active agent or its derivative which contain an organic acid functional group or metal salt thereof. The first coating is covalently bonded to the second coating through reaction of the excess cross-linking agent and the organic acid functional groups on the bio-active coating.

In a further embodiment of the present invention there is provided a bio-active coating composition for rendering substrates bio-compatible. This composition includes an aqueous dispersion or emulsion of an organic acid functional group-containing polymer and an excess of a polyfunctional cross-linking agent which is reactive with the organic acid functional groups of the polymer. This composition also includes an aqueous solution or dispersion of a bio-active agent or its derivative which contain an organic acid functional group or metal salt thereof. The polymer is bonded to the organic acid functional groups on the bio-active agent through the unreacted excess polyfunctional cross-linking agent.

DETAILED DESCRIPTION OF THE INVENTION

For purposes of the present invention, the term "organic acid functional group" is meant to include any functional group which contains an organic acidic ionizable hydrogen. Examples of such functional groups include free carboxylic, free sulfonic, and free phosphoric acid groups, their metal salts and combinations thereof. Such metal salts include, for example, alkali metal salts like lithium, sodium and potassium salts; alkaline earth metal salts like calcium or magnesium salts; and quaternary amine salts of such acid groups, particularly quaternary ammonium salts.

In the present invention, the organic acid functional group-containing polymer of the first aqueous coating composition is selected based on the nature of the substrate to be coated. The polymer in the first coating composition may be a homo- or copolymer such as, for example, vinyl monomer units, polyurethanes, epoxy resins and combinations thereof. These classes are merely exemplary and other polymeric materials may be found to be useful. Preferably, the polymer in the first coating composition may include organic acid functional group-containing polyurethanes, polyacrylates, polymethacrylates, polyisocrotonates, epoxy resins, (meth) acrylateurethane copolymers and combinations thereof. More preferably, the polymer in the first coating composition includes homo- and copolymers having a substantial amount of organic acid functional groups in their structure. Not wishing to be bound by a particular theory, it is believed that the presence of organic acid functional groups in the polymer act as internal emulsifying agents. A specific class of polyurethanes which are useful in the first coating are the so-called water-borne polyurethanes. Particularly preferred examples of such polyurethanes are internally emulsified water-borne polyurethanes containing internal emulsifiers such as, for example, carboxylic acid, sulfonic acid and/or phosphoric acid groups, including salts of such groups.

Water-borne polyurethanes which are internally emulsified include, for example, those supplied under the trade name NeoRez by Zeneca Resins, including NeoRez-940, NeoRez-972, NeoRez-976 and NeoRez-981; those under the trade name Sancure, including Sancure 2026, Sancure 2710, Sancure 1601 and Sancure 899 by B. F. Goodrich; and those under the trade names Bayhydrol LS-2033, Bayhydrol LS-2100, Bayhydrol LS-2990 by Bayer AG.

Another example of a type of polymer useful in the first coating composition is the (meth)acrylate-urethane copolymers, including (meth)acrylic urethane copolymer dispersions supplied under the trade names NeoPac E-106, NeoPac E-121, NeoPac E-130 and NeoRez R-973 by Zeneca Resins.

The concentration of the polymer in the first coating is from about 1% to about 60% by weight, and preferably from about 1% to about 40% by weight. These percent weight values are calculated based on the amount of solid polymer compared to the total weight of the first coating.

The first coating also includes one or more polyfunctional cross-linking agents that are reactive with organic acid functional groups. In the present invention, preferred polyfunctional cross-linking agents include polyfunctional aziridines and polyfunctional carbodiimides.

In the present invention, other cross-linking agents may also be used which include, for example, commercially available preparations sold by Zeneca Resins under the trade name NeoCryl CX 100 and those preparations sold by EIT Industries under the trade name XAMA-7. A commercially available polyfunctional carboimide which is also useful in the present invention is Ucarlink XL-29SE, sold by Union Carbide.

Among the polyfunctional aziridines useful in the present invention are the trifunctional aziridines of the following formula:

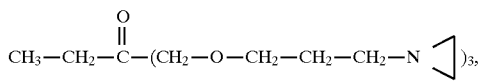

Preferably, the cross-linking agent has more than two functional groups per molecule. Furthermore, the present invention also encompasses a combination of different polyfunctional cross-linking agents.

Not wishing to be bound by a particular theory, it is believed that the functional groups on the cross-linking agent serve at least two purposes. In particular, these groups serve to cross-link the first polymeric coating. Additionally, these groups participate in covalently bonding the second coating to the first coating through reaction with the excess organic acid functional groups on the bio-active agent. Thus, there must be sufficient functionality in the cross-linking agent, e.g. an excess of cross-linking agent, to accomplish both purposes. In particular, there must be a molar excess of cross-linking agent relative to the first coating to ensure that the first coating is substantially cross-linked, and that there are enough unreacted functional groups left on the cross-linking agent to covalently bond the bio-active agent to the first coating.

One indication that insufficient functional groups from the cross-linking agent are present is the inadequate bonding of the second layer to the substrate. This is evidenced by the lack of wear resistance of substrates treated with such a deficient first coating. Furthermore, such coatings are easily wiped off the substrate to which they are applied.

The concentration of the cross-linking agent in the first coating composition is in the range from about 0.2% to about 40% by weight solids content of the first coating, and preferably in the range from about 0.5% to about 20% by weight solids content of the first coating.

The first aqueous coating may include other conventional additives, such as for example, leveling agents, various stabilizers, pH adjustment agents, fillers, defoaming agents and the like, as long as such agents are compatible with the intended use of the coated substrate.

The first coating is applied to a substrate by conventional methods, including dipping and spraying. The first coating is then permitted to dry to obtain a continuous, substantially water-insoluble coating on the surface of the substrate. This coating includes functional groups on the cross-linking agent which are reactive with organic acid groups of the first coating. This dried first coating is contacted with a second aqueous coating which includes an aqueous solution or dispersion of an organic acid functional group-containing bio-active agent. The second coating may be applied over the first coating using the same or different techniques as the first coating. The second coating is then permitted to dry, thereby covalently bonding the organic acid functional group-containing bio-active agent to the first coating via the excess, unreacted functional groups of the cross-linking agent in the first coating. Optionally, the bio-active agent may be incorporated into the first coating in a non-covalent manner. The choice of whether to covalently bond the bio-active agent to the first coating is made with reference to the intended use of the device, the choice of bio-active agent and the composition of the first coating.

Bio-active agents useful in the present invention may be selected from a wide variety of materials provided that they contain at least one organic acid functional group in their structure which can react with the polyfunctional cross-linking agent and still retain bio-active function. Furthermore, in the case where a particular bio-active agent does not contain at least one organic acid functional group in its structure, a derivative thereof containing such an organic acid functional group is also encompassed by the present invention. The use and synthesis of such derivatives are within the knowledge of those skilled in the art.

Non-limiting classes of useful bio-active agents of the present invention include antithrombogenic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulation agents, genetic agents, including hormones, such as estrogen, their homologues, analogs, derivatives, fragments, pharmaceutical salts and mixtures thereof. Other useful bio-active agents include for example, viral reactors and growth hormones such as Fibroblast Growth Factor and Transforming Growth Factor-β, their homologues, analogs, derivatives, fragments, pharmaceutical salts and mixtures thereof. One specific type of bio-active material useful in the present invention is the class of organic acid functional group-containing polysaccharides. For purposes of the present invention, such polysaccharides include linear and branched polymers of monosaccharides. The preferred polysaccharide bio-active agents of the present invention are glycosaminoglycans (hereinafter "GAGs") . Glycosaminoglycans are unbranched polysaccharide chains of repeating disaccharide units. One of the repeating disaccharide units is usually an amino sugar (N-acetylglucosamine or N-acetylgalactosamine) which can be sulfated. The second sugar of the disaccharide unit is usually a uronic acid, such as for example, glucuronic or iduronic acid. Because there are sulfate or carboxyl groups on most of their sugar residues, GAGs are highly negatively charged and are ideal for covalently bonding to the first coating layers via the excess, unreacted functional groups on the cross-linking agent. GAGs which are useful as bio-active agents in the present invention include, for example, heparin, hirudin, heparin sulfate, hyaluronic acid, chondroitin sulfate, dermatan sulfate, keratan sulfate, EPA, prostoctein, reopro, integrin, lytic agents including urokinase and streptokinase, their homologs, analogs, fragments, derivatives and pharmaceutical salts thereof. Other GAG containing molecules are also contemplated by the present invention, for example GAG-containing proteins, such as proteglycans.

Moreover, the bio-active agent of the present invention can also include organic acid functional group-containing antibiotics. For purposes of the present invention, such antibiotics include penicillins, cephalosporins, vancomycins, aminoglycosides, quinolones, polymyxins, erythromycins, tetracyclines, chloramphenicols, clindamycins, lincomycins, sulfonamides their homologs, analogs, fragments, derivatives, pharmaceutical salts and mixtures thereof.

Additionally, the bio-active agent of the present invention can also include organic acid functional group-containing anti-tumor agents. For purposes of the present invention, such anti-tumor agents include paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including estrogen, tamoxifen and flutamide their homologs, analogs, fragments, derivatives, pharmaceutical salts and mixtures thereof.

Still further, the bio-active agent of the present invention can include organic acid functional group-containing anti-viral agents. For purposes of the present invention, such anti-viral agents include amantadines, rimantadines, ribavirins, idoxuridines, vidarabines, trifluridines, acyclovirs, ganciclovirs, zidovudines, foscarnets, interferons their homologs, analogs, fragments, derivatives, pharmaceutical salts and mixtures thereof.

In certain cases, such bio-active agents may also become lubricous upon contact with an aqueous medium. Such lubricity will depend on a number of factors, including the type of bio-active agent, its molecular weight, the exposure level to the aqueous medium, as well as the presence of agents which facilitate wetting. In the present invention, the molecular weight of the bio-active agent can vary from fewer than 500 for paclitaxel to about 3,000 to about 30,000 for heparin to an excess of 8,000,000 for hyaluronic acid.

The concentration of the bio-active agent in the second coating composition will typically be from about 0. 1% by weight, preferably from about 50% by weight, calculated as solids of bio-active agent compared to the total weight of the second coating composition.

In one embodiment of the present invention, the functional groups of the cross-linking agent react with the organic acid functional groups of the polymer in the first coating and the organic acid functional groups of the bio-active agent at a temperature below 120° C. Preferably, these reactions take place between about 10° C. to about 70° C. The drying step for the second coating is chosen based on the substrate and the compositions used in the first and second coatings. Many bio-active agents are temperature sensitive and extreme care must be taken in selecting the appropriate drying temperatures with such agents. For example, when heparin is the bio-active agent, the drying temperature should be no greater than about body temperature.

The selection of the appropriate drying temperature is within the skill of the art given the properties of the substrate and the compositions in the first and second coatings. Preferably, the drying step takes place well below 120° C. If desired, however, and compatible with the nature of the substrate to be coated, higher temperatures may be used, such as for example, when the substrate is metal. Nevertheless, the present invention is designed to be used in coating temperature-sensitive substrates. Thus, the first and second coatings are preferably dried at low temperatures, particularly at ambient or room temperatures, such as for example, at or between about 15° C. and about 35° C. In many cases, drying at about room temperature for about 12 hours will be adequate.

Obviously, the drying time will depend on the drying temperature used, higher drying temperatures requiring shorter drying times and lower drying temperatures requiring longer drying times. As set forth above, it is within the knowledge of a person skilled in the art to determine a suitable combination of drying temperatures and drying times for a specific coating and substrate.

Furthermore, the organic acid functional groups of the cross-linking agent do not necessarily have to have the same reactivity towards the organic acid functional groups of the polymer and bio-active agent in the first and second coatings, respectively. Moreover, the selection of drying conditions will be made with these reactivities in mind.

The bio-active coatings of the present invention may be used to coat a wide range of different substrates. In particular, the bio-active coatings are especially suited for coating at least a portion of a surface of a medical article for use in or on the body, particularly catheters, guidewires, introducer sheaths, trocars and the like, or parts of such articles. More particularly, these coatings may be used to coat endoprostheses including for example, grafts, stents and graft-stent devices. Furthermore, these coatings can be used to coat many different substrates, such as for example, polymeric substrates, non-polymeric substrates, such as metals, and combinations thereof.

For purposes of the present invention, polymeric substrates which may be used include, for example, olefin polymers, particularly polyethylene, polypropylene, polyvinylchloride, polytetrafluoroethylene (PTFE), polyvinylacetate, and polystyrene; polyesters, particularly poly(ethylene terephthalate); polyurethanes; polyureas; silicone rubbers; polyamides, particularly nylons; polycarbonates; polyaldehydes; natural rubbers; polyether-ester copolymers such as Hytrel™ and Anitel™; polyether-amide copolymers such as Pebax™; and styrene-butadiene copolymers. Preferably, the polymeric substrate is made from poly(ethylene terephthalate), polyurethane, polyethylene, nylon 6, nylon 11, a polyether-ester copolymer or a polyether-amide copolymer. Shape-memory polymers are also contemplated. The substrate can, of course, be made from other polymers depending upon the intended use thereof and the composition of the first and second coatings. Such a choice of substrate materials is within the knowledge of one skilled in the art.

As set forth above, non-polymeric substrates may also be used in the present invention. These non-polymeric substrates include, for example ceramics, metals, glasses and the like. Furthermore, the substrates of the present invention may include a combination of one or more polymers and/or one or more non-polymers. Examples of metals employed in medical devices include, without limitation, stainless steel, superelastic materials (shape-memory) such as nitinol, gold, silver, titanium, tantulum, platinum and alloys thereof.

In another embodiment of the present invention, a medical device having a bio-active coating on at least a portion of a surface thereof is provided for use in conjunction with a body. The bio-active coating includes a first substantially water-insoluble coating layer formed from an aqueous dispersion or emulsion of an organic functional group-containing polymer and an excess of a polyfunctional cross-liking agent, each of which is described above. As set forth previously, the cross-linking agent is reactive with the organic acid groups of the polymer.

The bio-active composition also includes a second coating of an aqueous solution or dispersion which contains an organic acid functional group-containing bio-active agent, as described hereinabove. The first coating is covalently bonded to the second coating through the excess cross-linking agent and the organic acid functional groups on the bio-active coating.

In a further embodiment of the present invention, there is provided a bio-active coating composition for rendering substrates bio-compatible. This coating composition includes an aqueous dispersion or emulsion of an organic acid functional group-containing polymer and an excess of a polyfunctional cross-linking agent, each of which is described above. This cross-linking agent is reactive with the organic acid functional groups of the polymer. There is also provided an aqueous solution or dispersion of an organic acid functional group-containing bio-active agent, as previously described. The polymer is bonded to the organic acid functional groups on the bio-active agent through the unreacted, excess polyfunctional cross-linking agent.

The invention will now be further illustrated in the following non-limiting examples representing presently preferred embodiments of the invention.

EXAMPLE 1

A first coating composition is prepared by adding the following ingredients successively to a glass beaker under proper agitation until thoroughly mixed.

NeoRez R981: 250 ml

Water: 250 ml 0.5% Fluorad FC-129 stock solution: 10 ml (prepared by diluting 1 ml Fluorad FC-129 in 100 ml of water)

34% $NH_4OH$: 4 ml

NeoCryl CX 100: 20 ml

NeoRez R981 (from Zeneca Resins) is a polyester-based, aliphatic water-borne polyurethane containing carboxylic acid groups as internal emulsifier, which is stabilized by triethylamine (TEA) and has a solids content of 32% and a pH of 7.5–9.0 at 25° C. It contains a 5.3% N-methylpyrrolidone as cosolvent. NeoCryl CX 100 (from Zeneca Resins) is a polyfunctional aziridine crosslinking agent. Fluorad FC-129 (from 3M) is added as a leveling agent. Ammonium hydroxide is used to adjust the pH of the solution.

A second coating composition, as follows, is prepared:

1.2% aqueous solution of Sodium Heparin (Abbott): 400 ml

The above solution is prepared by adding an appropriate amount of heparin powder to water under agitation for several hours to obtain a clear homogeneous solution.

A substrate is prepared by extruding a blend of two grades of polyether-ester block copolymer ARNITEL EM 740 and EM630 (from Akzo) with $BaSO_4$, into a tube. The tube is dipped into the first coating composition prepared above and dried at ambient temperature (room temperature) for 40 minutes. Then the tube is dipped in the second coating composition and dried at ambient temperature over night to form a continuous coating of the heparin on the surface of the substrate. The coated surface shows very good anti-thrombogenic effect when contacted with blood. Furthermore, the coating has very good durability while still retaining its bio-activity. The coating is strongly retained on the surface even under the application of strong forces.

EXAMPLE 2

In the same manner as in Example 1, a first coating composition is prepared using the following ingredients:

Sancure 2710: 250 ml

Water: 100 ml

NeoCryl CX 100: 10 ml

Sancure 2710 (from B. F. Goodrich) is an aliphatic polyurethane dispersion containing carboxylic acid groups as internal emulsifier and being stabilized by TEA. The dispersion has a solids content of about 40%, a pH of 8.3 and a viscosity of 1,000 cps.

A second coating composition is prepared in the same manner as in Example 1:

1.2% sodium heparin (Abbott) aqueous solution

Endoprostheses, including a textile (PET) vascular graft, a vascular stent and a vascular graft-stent combination are each coated with the above coating compositions in the following manner. The endoprostheses are coated with the first coating composition by dipping. The endoprostheses are then dried at ambient temperature for 30 minutes. Next, the prostheses are dipped in the second coating composition and dried at ambient temperature over night. The resultant dried coating is sterilized by electron beams at a dose of 2×25 KGray.

The coated endoprostheses each show excellent anti-thrombogenic activity and lubricity when contacted with blood. Furthermore, the coating has very good durability while still retaining its bio-activity.

EXAMPLE 3

First and second coating compositions are prepared as described in Example 2, with the exception that heparin sulfate is substituted for heparin in the second coating. Endoprostheses are coated as described in Example 2. The coated endoprostheses show excellent anti-thrombogenic activity and lubricity when contacted with blood. Furthermore, the coating has very good durability while still retaining its bio-activity.

EXAMPLE 4

First and second coating compositions are prepared as described in Example 2 except that sodium hyaluronate (hyaluronic acid) is substituted for heparin in the second coating. Endoprostheses are coated as described in Example 2. The coated endoprostheses show excellent anti-thrombogenic activity and lubricity when contacted with blood. Furthermore, the coating has very good durability while still retaining its bio-activity.

EXAMPLE 5

First and second coating compositions are prepared as described in Example 2 except that chondroitin sulfate is substituted for heparin in the second coating. Endoprostheses are coated as described in Example 2. The coated endoprostheses show excellent anti-thrombogenic activity and lubricity when contacted with blood. Furthermore, the coating has very good durability while still retaining its bio-activity.

EXAMPLE 6

First and second coating compositions are prepared as described in Example 2 except that dermatan sulfate is substituted for heparin in the second coating. Endoprostheses are coated as described in Example 2. The coated endoprostheses show excellent anti-thrombogenic activity and lubricity when contacted with blood. Furthermore, the coating has very good durability while still retaining its bio-activity.

EXAMPLE 7

First and second coating compositions are prepared as described in Example 2 except that keratan sulfate is substituted for heparin in the second coating. Endoprostheses are coated as described in Example 2. The coated endoprostheses show excellent anti-thrombogenic activity and lubricity when contacted with blood. Furthermore, the coating has very good durability while still retaining its bio-activity.

EXAMPLE 8

A first coating composition is prepared as described in Example 1 using the following ingredients:

Bayhydrol LS-2033: 250 ml

Water: 250 ml 0.5 Fluorad FC-129 stock solution: 10 ml

34% $NH_4OH$: 4 ml

NeoCryl CX 100: 20 ml

Bayhydrol LS-2033 (from Bayer A.G.) is a water-borne polyurethane which is stabilized by sulfonate groups. The water-borne polyurethane as supplied has a pH of 6.5–7.5, and the sulfonate groups are in sodium salt form. The polyurethane has a solids content of 40%.

A second coating composition is prepared as described in Example 1 using the following ingredients:

Heparin: 400 ml of Sodium Heparin (Abbott) in 1% Versicol WN23

Streptomycin: 1.0 ml of an aqueous solution containing 10,000 Units of Streptomycin Sulfate A polyurethane catheter is dipped in the first coating composition and dried in an over at 60° C. for 10 minutes. Then the catheter is dipped in the second coating composition, dried in an oven at 60° C. for 10 minutes and dipped in the second coating composition once more, after which it is dried at ambient temperature over night. The coated catheter shows excellent anti-thrombogenicity and antibacterial properties, as well as, good lubricity when contacted with blood.

EXAMPLE 9

Using the same coating procedures as described in Example 1, a stainless steel stent is coated with the following coating compositions.

First coating composition:

NeoPacE121: 250ml

Water: 100 ml

34% $NH_4OH$: 2 ml

NeoCryl CX 100: 16 ml

Second coating composition:

1.0% aqueous solution of Sodium Heparin (Abbot): 400 ml

The coated stent shows excellent anti-thrombogenicity when contacted with blood.

EXAMPLE 10

Using the same coating procedures as described in Example 1, a PET endoprosthesis is coated with the following coating compositions:

First coating composition:
Bayhydrol LS 2033: 200 ml
NeoRez R-940: 100 ml
Triethylamine: 2 ml
Water: 200 ml
NeoCryl CX 100: 10 ml
Second coating composition:
0.8% sodium heparin (Abbott) aqueous solution: 400 ml
The coated endoprosthesis shows excellent anti-thrombogenicity when contacted with blood.

EXAMPLE 11

A glass plate is coated with the following coating compositions as described below:
First coating composition:
Sancure 899: 200 ml
NeoPac E121: 100 ml
Acrysol TT-615: 1 ml (prediluted with equal weight of water)
SAG 710: 1 ml
34% $NH_4OH$: 4 ml
Second coating composition:
1% Sodium Heparin (Abbott) aqueous solution: 400 ml
The first coating composition is brushed onto the glass plate and dried at ambient temperature for 1 hour. Then, the second coating composition is sprayed onto the precoated glass surface and dried at ambient temperature over night. The coated glass shows excellent anti-thrombogenicity when contacted with blood.
Acrysol TT-615 is a thickener available from Rohm and Haas Company, and SAG 710 is a defoaming agent available from OSI Specialties, Inc.

EXAMPLE 12

First coating composition:
Sancure 899: 250 ml
0.5% Fluorad FC-129 stock solution: 10 ml
34% $NH_4OH$: 4 ml
Water: 200 ml
Ucarlink XL-29SE: 40 ml
Second coating composition:
1% sodium heparin (Abbott) aqueous solution: 400 ml
A graft made from polyurethane is dipped in the first coating composition and dried at ambient temperature for 40 minutes. Then, the graft is dipped in the second coating composition, dried at ambient temperature for 30 minutes and then dipped in the second coating composition once more. The coating is sterilized by EtO (ethylene oxide) sterilization. The coated graft shows excellent anti-thrombogenicity when contacted with blood.
Ucarlink XL-29SE is a polyfunctional carboimide, available from Union Carbide.

EXAMPLE 13

A PET endoprosthesis is coated with the following coating compositions:
First coating composition:
NeoPac E121: 250 ml
Water: 250 ml
Ucarlink XL-29SE: 40 ml
Second coating composition:
1% sodium heparin (Abbott) aqueous solution: 400 ml
First coating composition: 1 ml
The endoprosthesis is dipped in the first coating composition and air dried for 30 minutes. Then, the precoated endoprosthesis is dipped in the second coating composition and air dried for 30 minutes followed by drying at 60° C. for 24 hours. The coated endoprosthesis shows excellent anti-thrombogenicity when contacted with blood.

The invention being thus described, it will be obvious that the same may be varied in many ways. Such variations are not to be regarded as a departure from the spirit and scope of the invention and, all such modifications are intended to be included within the scope of the following claims.

What is claimed is:

1. A method of enhancing the biocompatibility of a substrate by providing said substrate with a continuous bio-active surface coating comprising:
    a) applying to said substrate a first coating comprising an aqueous dispersion or emulsion of (i) a polymer containing an organic acid functional group and (ii) an excess of a polyfunctional cross-linking agent which is reactive with said organic acid groups of said polymer, permitting said first coating to dry in order to cross-link and render said first coating substantially water-insoluble, wherein unreacted polyfunctional cross-linking agent remains present in said cross-linked first coating;
    b) forming said continuous bio-active surface coating on said substrate by contacting said dried first coating layer with a second coating of an aqueous solution or dispersion of a bio-active agent containing an organic acid functional group or metal salt thereof; and
    c) drying said first and second coatings to covalently bond said organic acid functional groups of said bio-active agent to said polymer through said excess unreacted polyfunctional cross-linking agent.

2. The method of claim 1, wherein said organic acid functional groups of said polymer and said bio-active agent are independently selected from the group consisting of free carboxylic acid, free sulfonic acid, free phosphoric acid, and combinations thereof.

3. The method of claim 1, wherein said metal salts are alkali metal salts and quaternary amine salts.

4. The method of claim 1, wherein said polyfunctional cross-linking agent has more than two functional groups per molecule.

5. The method of claim 1, wherein said polymer is one of an organic acid functional group-containing homo- and copolymer.

6. The method of claim 1, wherein said polymer is selected from the group consisting of polyurethanes, polyacrylates, poly(meth)acrylates, polyisocrotonates, epoxy resins, (meth)acrylate-urethane copolymers and combinations thereof.

7. The method of claim 1, wherein said polymer is an (meth)acrylate-urethane copolymer.

8. The method of claim 1, wherein said polymer is a polyurethane.

9. The method according to claim 1, wherein said bio-active agent is selected from the group consisting of anti-thrombogenic agents, antibiotic agents, anti-tumor agents, antiviral agents, anti-angiogenic agents, angiogenic agents, anti-mitotic agents, anti-inflammatory agents, angiostatin agents, endostatin agents, cell cycle regulatory agents, genetic agents, growth hormones and mixtures thereof.

10. The method according to claim 1, wherein said bio-active agent is an organic acid functional group-containing polysaccharide.

11. The method according to claim 10, wherein said polysaccharide is a glycosaminoglycan.

12. The method according to claim 11, wherein said glycosaminoglycan is selected from the group consisting of heparin, hirudin, heparin sulfate, hyaluronic acid, chondroitin sulfate, dermatan sulfate, keratin sulfate, prostoctein, reopro, integrin and chemically-modified equivalents thereof.

13. The method according to claim 1, wherein the concentration of said polymer in said first coating is from about 1% to about 60% by weight solids content.

14. The method according to claim 1, wherein the concentration of said polymer in said first coating is from about 1% to about 40% by weight solids content.

15. The method according to claim 1, wherein the concentration of said polyfunctional cross-linking agent in said first coating is from about 0.2% to about 40% by weight solids content of said first coating.

16. The method according to claim 1, wherein said first layer is covalently bonded to said second layer via said polyfunctional cross-linking agent at a temperature below about 120° C.

17. The method according to claim 1, wherein said first layer is covalently bonded to said second layer via said polyfunctional cross-linking agent at a temperature between about 10° C. and about 70° C.

* * * * *